(12) United States Patent
Boucher

(10) Patent No.: US 8,691,790 B2
(45) Date of Patent: Apr. 8, 2014

(54) THERAPY OF NEUROLOGICAL INFLAMMATORY DISEASES WITH (5'-DEOXY-5'-ADENOSYL) COBAMAMIDE, RECOMBINANT HUMAN GROWTH HORMONE, INTERLEUKINS IL-1, IL-6, IL-11, EPIDERMAL GROWTH FACTOR, AND PHYSIOTHERAPY

(76) Inventor: James Layne Boucher, Stephenville, TX (US)

( * ) Notice: Subject to any disclaimer, the term of this patent is extended or adjusted under 35 U.S.C. 154(b) by 771 days.

(21) Appl. No.: 12/460,946

(22) Filed: Jul. 27, 2009

(65) Prior Publication Data
US 2011/0020311 A1    Jan. 27, 2011

(51) Int. Cl.
*A01N 43/04*    (2006.01)

(52) U.S. Cl.
USPC ............. 514/52; 424/94.5; 435/193; 514/7.6; 514/8.4; 514/11.4

(58) Field of Classification Search
None
See application file for complete search history.

(56) References Cited

U.S. PATENT DOCUMENTS

| | | |
|---|---|---|
| 3,849,550 A | 11/1974 | Teitelbaum et al. |
| 4,631,211 A | 12/1986 | Houghten |
| 5,045,190 A | 9/1991 | Carbonell et al. |
| 5,800,808 A | 9/1998 | Konfino et al. |
| 5,981,589 A | 11/1999 | Konfino et al. |
| 6,054,430 A | 4/2000 | Konfino et al. |
| 6,342,476 B1 | 1/2002 | Konfino et al. |
| 6,362,161 B1 | 3/2002 | Konfino et al. |
| 6,410,697 B1 | 6/2002 | Berg |
| 6,620,847 B2 | 9/2003 | Konfino et al. |
| 6,869,600 B1 * | 3/2005 | Sadoul et al. ................ 424/85.4 |
| 6,894,033 B2 | 5/2005 | Cruz et al. |
| 6,908,611 B2 | 6/2005 | Cruz et al. |
| 6,939,539 B2 | 9/2005 | Konfino et al. |
| 7,199,098 B2 | 4/2007 | Konfino et al. |
| 7,368,531 B2 | 5/2008 | Rosen et al. |

OTHER PUBLICATIONS

Kira et al., Internal Medicine, 1994, vol. 33, p. 82-86.*
KEGG compound C00194, downloaded from the website 2012.*
Aguilar et al., The EFSA Journal, 2008, 815, p. 1-21.*
Miller et al., Journal of Neurological Sciences, 2005, vol. 233, p. 93-97.*
Wiles et al., J Neurol. Neurosurg Psychiatry, 2001, vol. 70, p. 174-179.*
Amanda Kimble,Staff Writer, "Back on his feet," Stephenville Empire Tribune, Published: Sunday, Apr. 19, 2009 3:42 PM CDT.

* cited by examiner

*Primary Examiner* — Kade Ariani

(57) ABSTRACT

A novel etiological hypothesis for Multiple Sclerosis (MS) is proposed describing autoimmune attack of ATP: Cob(I) alamin adenosyltransferase (ATR) thereby inhibiting synthesis of (5'-deoxy-5'-adenosyl)cobamide (referred to as 5'-deoxyadenosylcobalmin or AdoCbl) from Vitamin B 12 providing a basis for therapeutic design and diagnostic methods. Pharmaceutical compositions for therapy of MS, inflammatory neurological diseases and neurodegenerative diseases utilizing AdoCbl, growth hormones, immunomodulators, interleukins, other therapeutic agents, and physiotherapy are also described.

9 Claims, No Drawings

SEQUENCE LISTING

<160> NUMBER OF SEQ ID NOS: 41

<210> SEQ ID NO 1
<211> LENGTH: 55
<212> TYPE: PRT
<213> ORGANISM: Homo sapiens
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-15196
<307> DATE: 2006-12-26
<313> RELEVANT RESIDUES IN SEQ ID NO: (1)..(55)

<400> SEQUENCE: 1

Ile Pro Lys Ile Tyr Thr Lys Thr Gly Asp Lys Gly Phe Ser Ser Thr
1               5                   10                  15

Phe Thr Gly Glu Arg Arg Pro Lys Asp Asp Gln Val Phe Glu Ala Val
            20                  25                  30

Gly Thr Thr Asp Glu Leu Ser Ser Ala Ile Gly Phe Ala Leu Glu Leu
        35                  40                  45

Val Thr Glu Lys Gly His Thr
    50                  55

<210> SEQ ID NO 2
<211> LENGTH: 67
<212> TYPE: PRT
<213> ORGANISM: Homo sapiens
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry.
<304> VOLUME: 45
<305> ISSUE: 51
<306> PAGES: 15188-96
<307> DATE: 2006-12-26
<313> RELEVANT RESIDUES IN SEQ ID NO: (110)..(176)

<400> SEQUENCE: 2

Cys Thr Leu Gln Asp Val Gly Ser Ala Leu Ala Thr Pro Cys Ser Ser
1               5                   10                  15

Ala Arg Glu Ala His Leu Lys Tyr Thr Thr Phe Lys Ala Gly Pro Ile
            20                  25                  30

Leu Glu Leu Glu Gln Trp Ile Asp Lys Tyr Thr Ser Gln Leu Pro Pro
        35                  40                  45

Leu Thr Ala Phe Ile Leu Pro Ser Gly Gly Lys Ile Ser Ser Ala Leu
    50                  55                  60

His Phe Cys
65

<210> SEQ ID NO 3
<211> LENGTH: 9
<212> TYPE: PRT
<213> ORGANISM: Homo sapiens
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96

```
<307> DATE: 2006-12-26
<313> RELEVANT RESIDUES IN SEQ ID NO: (186)..(194)

<400> SEQUENCE: 3

Arg Ala Val Cys Arg Arg Ala Glu Arg
1               5

<210> SEQ ID NO 4
<211> LENGTH: 5
<212> TYPE: PRT
<213> ORGANISM: Homo sapiens
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (190)..(194)

<400> SEQUENCE: 4

Arg Arg Ala Glu Arg
1               5

<210> SEQ ID NO 5
<211> LENGTH: 7
<212> TYPE: PRT
<213> ORGANISM: Homo sapiens
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (195)..(201)

<400> SEQUENCE: 5

Arg Val Val Pro Leu Val Gln
1               5

<210> SEQ ID NO 6
<211> LENGTH: 49
<212> TYPE: PRT
<213> ORGANISM: Homo sapiens
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (204)..(252)

<400> SEQUENCE: 6

Met Gly Glu Thr Asp Ala Asn Val Ala Lys Phe Leu Asn Arg Leu Ser
1               5                   10                  15

Asp Tyr Leu Phe Thr Leu Ala Arg Tyr Ala Ala Met Lys Glu Gly Asn
                20                  25                  30

Gln Glu Lys Ile Tyr Lys Lys Asn Asp Pro Ser Ala Glu Ser Glu Gly
            35                  40                  45

Leu
```

-continued

```
<210> SEQ ID NO 7
<211> LENGTH: 50
<212> TYPE: PRT
<213> ORGANISM: Pyrococcus horikoshi
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 1588-96
<307> DATE: 2006-12-26
<313> RELEVANT RESIDUES IN SEQ ID NO: (1)..(50)

<400> SEQUENCE: 7

Met Arg Ile Thr Thr Lys Val Gly Asp Lys Gly Ser Thr Arg Leu Phe
1               5                   10                  15

Gly Gly Glu Glu Val Trp Lys Asp Ser Pro Ile Ile Glu Ala Asn Gly
            20                  25                  30

Thr Leu Asp Glu Leu Thr Ser Phe Ile Gly Glu Ala Lys His Tyr Val
        35                  40                  45

Val Asp
    50

<210> SEQ ID NO 8
<211> LENGTH: 23
<212> TYPE: PRT
<213> ORGANISM: Pyrococcus horikoshi
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (51)..(73)

<400> SEQUENCE: 8

Glu Glu Met Lys Gly Ile Leu Glu Glu Ile Gln Asn Asp Ile Tyr Lys
1               5                   10                  15

Ile Met Gly Glu Ile Gly Ser
            20

<210> SEQ ID NO 9
<211> LENGTH: 6
<212> TYPE: PRT
<213> ORGANISM: Pyrococcus horikoshi
<300> PUBLICATION INFORMATION:
<301> AUTHORS: Schubert HL, Hill CP
<302> TITLE: Structure of ATP-bound human ATP:cobalamin
     adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (74)..(79)

<400> SEQUENCE: 9

Lys Gly Lys Ile Glu Gly
1               5

<210> SEQ ID NO 10
<211> LENGTH: 16
<212> TYPE: PRT
<213> ORGANISM: Pyrococcus horikoshi
```

```
<300> PUBLICATION INFORMATION:
<301> AUTHORS: Schubert HL, Hill CP
<302> TITLE: Structure of ATP-bound human ATP:cobalamin
       adenosyltransferase
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (80)..(95)

<400> SEQUENCE: 10

Ile Ser Glu Glu Arg Ile Lys Trp Leu Glu Gly Leu Ile Ser Arg Tyr
1               5                   10                  15

<210> SEQ ID NO 11
<211> LENGTH: 38
<212> TYPE: PRT
<213> ORGANISM: Pyrococcus horikoshi
<300> PUBLICATION INFORMATION:
<301> AUTHORS: Schubert HL, Hill CP
<302> TITLE: Structure of ATP-bound human ATP:cobalamin
       adenosyltransferase
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (96)..(133)

<400> SEQUENCE: 11

Glu Phe Gly Ile Gly Lys Glu Ala Leu Val Tyr Leu Asn Arg Leu Ser
1               5                   10                  15

Asp Leu Leu Phe Leu Leu Ala Arg Val Ile Glu Ile Glu Lys Asn Lys
            20                  25                  30

Leu Lys Glu Val Arg Ser
        35

<210> SEQ ID NO 12
<211> LENGTH: 56
<212> TYPE: PRT
<213> ORGANISM: Mycobacterium tuberculosis
<300> PUBLICATION INFORMATION:
<301> AUTHORS: Schubert HL, Hill CP
<302> TITLE: Structure of ATP-bound human ATP:cobalamin
       adenosyltransferase
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (1)..(55)

<400> SEQUENCE: 12

Met Ala Val His Leu Thr Arg Ile Tyr Thr Arg Thr Asp Gly Gly Asp
1               5                   10                  15

Thr Thr Gly Leu Ser Asp Met Ser Arg Val Ala Lys Thr Asp Ala Arg
            20                  25                  30

Leu Val Ala Tyr Ala Asp Gln Asp Glu Ala Asn Ala Ala Ile Gly Ala
        35                  40                  45

Ala Leu Ala Leu Gly His Pro Asp
    50                  55

<210> SEQ ID NO 13
<211> LENGTH: 25
<212> TYPE: PRT
<213> ORGANISM: Mycobacterium tuberculosis
```

```
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (56)..(80)

<400> SEQUENCE: 13

Thr Gln Ile Thr Asp Val Leu Arg Gln Ile Gln Asn Asp Leu Phe Asp
1               5                   10                  15

Ala Gly Ala Asp Leu Ser Thr Pro Ile
            20                  25

<210> SEQ ID NO 14
<211> LENGTH: 112
<212> TYPE: PRT
<213> ORGANISM: Mycobacterium tuberculosis
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (81)..(192)

<400> SEQUENCE: 14

Val Glu Asn Pro Lys His Pro Pro Leu Arg Ile Ala Gln Ser Tyr Ile
1               5                   10                  15

Asp Arg Leu Glu Gly Trp Cys Asp Ala Tyr Asn Ala Gly Leu Pro Ala
            20                  25                  30

Leu Lys Ser Phe Val Leu Pro Gly Gly Ser Pro Leu Ser Ala Leu Leu
        35                  40                  45

His Val Ala Arg Thr Val Val Arg Arg Ala Glu Arg Ser Ala Trp Ala
    50                  55                  60

Ala Val Asp Ala His Pro Glu Gly Val Ser Val Leu Pro Ala Lys Tyr
65                  70                  75                  80

Leu Asn Arg Leu Ser Asp Leu Leu Phe Ile Leu Ser Arg Val Ala Asn
                85                  90                  95

Pro Asp Gly Asp Val Leu Trp Arg Pro Gly Gly Asp Arg Thr Ala Ser
            100                 105                 110

<210> SEQ ID NO 15
<211> LENGTH: 47
<212> TYPE: PRT
<213> ORGANISM: Thermoplasma acidphilum
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (1)..(46)
```

-continued

<400> SEQUENCE: 15

Met Phe Thr Arg Arg Gly Asp Gln Gly Glu Thr Asp Leu Ala Asn Arg
1               5                   10                  15

Ala Arg Val Gly Lys Asp Ser Pro Val Val Glu Val Gln Gly Thr Ile
            20                  25                  30

Asp Glu Leu Asn Ser Phe Ile Gly Tyr Ala Leu Val Leu Ser Arg
        35                  40                  45

<210> SEQ ID NO 16
<211> LENGTH: 24
<212> TYPE: PRT
<213> ORGANISM: Thermoplasma acidphilum
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (47)..(70)

<400> SEQUENCE: 16

Trp Asp Asp Ile Arg Asn Asp Leu Phe Arg Ile Gln Asn Asp Leu Phe
1               5                   10                  15

Val Leu Gly Glu Asp Val Ser Thr
            20

<210> SEQ ID NO 17
<211> LENGTH: 6
<212> TYPE: PRT
<213> ORGANISM: Thermoplasma acidphilum
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (71)..(76)

<400> SEQUENCE: 17

Gly Gly Lys Gly Arg Thr
1               5

<210> SEQ ID NO 18
<211> LENGTH: 57
<212> TYPE: PRT
<213> ORGANISM: Thermoplasma acidphilum
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (78)..(134)

<400> SEQUENCE: 18

Val Thr Arg Glu Met Ile Asp Tyr Leu Glu Ala Arg Val Lys Glu Met
1               5                   10                  15

Lys Ala Glu Ile Gly Lys Ile Glu Leu Phe Val Val Pro Gly Gly Ser
            20                  25                  30

-continued

Val Glu Ser Ala Ser Leu His Met Ala Arg Ala Val Ser Arg Arg Leu
            35                  40                  45

Glu Arg Arg Ile Val Ala Ala Ser Lys
        50                  55

<210> SEQ ID NO 19
<211> LENGTH: 44
<212> TYPE: PRT
<213> ORGANISM: Thermoplasma acidphilum
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (135)..(178)

<400> SEQUENCE: 19

Leu Thr Glu Ile Asn Lys Asn Val Leu Ile Tyr Ala Asn Arg Leu Ser
1               5                   10                  15

Ser Ile Leu Phe Met His Ala Leu Ile Ser Asn Lys Arg Leu Asn Ile
            20                  25                  30

Pro Glu Lys Ile Trp Trp Ser Ile His Arg Val Ser
        35                  40

<210> SEQ ID NO 20
<211> LENGTH: 44
<212> TYPE: PRT
<213> ORGANISM: Sulfolobus tokodaii (St1454)
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (1)..(43)

<400> SEQUENCE: 20

Phe Thr Lys Ser Gly Asp Asp Gly Asn Thr Asn Val Ile Asn Lys Arg
1               5                   10                  15

Val Gly Lys Asp Ser Pro Leu Asn Phe Leu Gly Asp Leu Asp Glu Leu
            20                  25                  30

Asn Ser Phe Ile Gly Phe Ala Ile Ser Lys Ile Pro
        35                  40

<210> SEQ ID NO 21
<211> LENGTH: 24
<212> TYPE: PRT
<213> ORGANISM: Sulfolobus tokodaii (St1454)
<220> FEATURE:
<221> NAME/KEY: misc_feature
<222> LOCATION: (4)..(4)
<223> OTHER INFORMATION: Xaa can be any naturally occurring amino acid
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (45)..(68)

-continued

```
<400> SEQUENCE: 21

Trp Glu Asp Xaa Lys Lys Asp Leu Glu Arg Val Gln Val Glu Leu Phe
1               5                   10                  15

Glu Ile Gly Glu Asp Leu Ser Thr
            20

<210> SEQ ID NO 22
<211> LENGTH: 5
<212> TYPE: PRT
<213> ORGANISM: Sulfolobus tokodaii (St1454)
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (69)..(73)

<400> SEQUENCE: 22

Gln Ser Lys Lys Lys
1               5

<210> SEQ ID NO 23
<211> LENGTH: 58
<212> TYPE: PRT
<213> ORGANISM: Sulfolobus tokodaii (St1454)
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (75)..(127)

<400> SEQUENCE: 23

Ile Asp Glu Lys Tyr Val Lys Trp Leu Glu Glu Arg Thr Val Glu Tyr
1               5                   10                  15

Arg Lys Glu Ser Gly Pro Val Lys Leu Phe Val Ile Pro Gly Gly Ser
            20                  25                  30

Glu Glu Ala Ser Val Leu His Val Thr Arg Ser Val Ala Arg Arg Val
        35                  40                  45

Glu Arg Asn Ala Val Lys Tyr Thr Lys Glu
    50                  55

<210> SEQ ID NO 24
<211> LENGTH: 43
<212> TYPE: PRT
<213> ORGANISM: Sulfolobus tokodaii (St1454)
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
```

-continued

```
<307> DATE: 2006-12-26
<313> RELEVANT RESIDUES IN SEQ ID NO: (130)..(172)

<400> SEQUENCE: 24

Leu Pro Glu Ile Asn Arg Xaa Ile Ile Val Tyr Leu Asn Arg Leu Ser
1               5                   10                  15

Ser Leu Leu Phe Ala Xaa Ala Leu Val Ala Asn Lys Arg Arg Asn Val
            20                  25                  30

Ser Glu Lys Ile Tyr Asp Ile Gly Lys Phe Trp
        35                  40

<210> SEQ ID NO 25
<211> LENGTH: 47
<212> TYPE: PRT
<213> ORGANISM: Sulfolobus tokodaii (St2180)
<300> PUBLICATION INFORMATION:
<301> AUTHORS: Schubert HL, Hill CP.
<302> TITLE: Structure of ATP-bound human ATP:cobalamin
      adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (1)..(47)

<400> SEQUENCE: 25

Trp Tyr Thr Gly Thr Gly Asp Lys Gly Lys Thr Lys Val Pro Ser Val
1               5                   10                  15

Gly Glu Val Trp Lys Asp Ser Glu Ile Val Lys Ala Leu Gly Asp Leu
            20                  25                  30

Asp Glu Leu Asn Ser Val Leu Gly Val Val Ser Ser Leu Tyr Pro
        35                  40                  45

<210> SEQ ID NO 26
<211> LENGTH: 22
<212> TYPE: PRT
<213> ORGANISM: Sulfolobus tokodaii (St2180)
<300> PUBLICATION INFORMATION:
<301> AUTHORS: Schubert HL, Hill CP
<302> TITLE: Structure of ATP-bound human ATP:cobalamin
      adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (48)..(69)

<400> SEQUENCE: 26

Glu Leu Ser Glu Val Ile Gln Lys Leu Gln Asn Asp Ile Phe Ser Ile
1               5                   10                  15

Ser Ser Glu Ile Ala Gly
            20

<210> SEQ ID NO 27
<211> LENGTH: 4
<212> TYPE: PRT
<213> ORGANISM: Sulfolobus tokodaii (St2180)
<220> FEATURE:
<221> NAME/KEY: misc_feature
<222> LOCATION: (3)..(3)
<223> OTHER INFORMATION: Xaa can be any naturally occurring amino acid
<300> PUBLICATION INFORMATION:
<301> AUTHORS: Schubert HL, Hill CP
<302> TITLE: Structure of ATP-bound human ATP:cobalamin
      adenosyltransferase.
<303> JOURNAL: Biochemistry
<304> VOLUME: 45
```

```
<305> ISSUE: 51
<306> PAGES: 15188-96
<307> DATE: 2006-12-26
<313> RELEVANT RESIDUES IN SEQ ID NO: (70)..(73)

<400> SEQUENCE: 27

Phe Asp Xaa Asn
1

<210> SEQ ID NO 28
<211> LENGTH: 57
<212> TYPE: PRT
<213> ORGANISM: Sulfolobus tokodaii (St2180)
<300> PUBLICATION INFORMATION:
<301> AUTHORS: Schubert HL, Hill CP
<302> TITLE: Structure of ATP-bound human ATP:cobalamin
      adenosyltransferase.
<303> JOURNAL: Biochemistry
<304> VOLUME: 45
<305> ISSUE: 51
<306> PAGES: 15199-96
<307> DATE: 2006-12-26
<313> RELEVANT RESIDUES IN SEQ ID NO: (74)..(130)

<400> SEQUENCE: 28

Phe Ser Asp Glu Lys Val Lys Gly Ile Glu Glu Leu Ile Thr Asn Tyr
1               5                   10                  15

Ser Lys Glu Leu Glu Pro Leu Arg Asn Phe Val Leu Pro Gly Gly His
            20                  25                  30

Ile Ala Ser Ser Phe Leu His Leu Ala Arg Ala Val Cys Arg Arg Ala
        35                  40                  45

Glu Arg Ser Val Val Thr Leu Leu Lys
    50                  55

<210> SEQ ID NO 29
<211> LENGTH: 40
<212> TYPE: PRT
<213> ORGANISM: Sulfolobus tokodaii (St2180)
<300> PUBLICATION INFORMATION:
<301> AUTHORS: Schubert HL, Hill CP
<302> TITLE: Structure of ATP-bound human ATP:cobalamin
      adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (131)..(170)

<400> SEQUENCE: 29

Glu Ser Lys Ala Lys Glu Val His Ala Lys Tyr Leu Asn Arg Ser Ser
1               5                   10                  15

Leu Leu Phe Val Leu Ala Leu Val Val Asn Lys Arg Thr Asn Asn Pro
            20                  25                  30

Asn Val Ile Trp Arg Gly Lys Asp
        35                  40

<210> SEQ ID NO 30
<211> LENGTH: 16
<212> TYPE: PRT
<213> ORGANISM: Bacillus subtilis
<300> PUBLICATION INFORMATION:
<301> AUTHORS: Schubert HL, Hill CP
<302> TITLE: Structure of ATP-bound human ATP:cobalamin
      adenosyltransferase.
<303> JOURNAL: Biochemistry
<304> VOLUME: 45
```

-continued

```
<305> ISSUE: 51
<306> PAGES: 15188-96
<307> DATE: 2006-12-26
<313> RELEVANT RESIDUES IN SEQ ID NO: (1)..(16)

<400> SEQUENCE: 30

Lys Leu Tyr Thr Lys Thr Gly Asp Lys Gly Gln Thr Gly Leu Val Gly
1               5                   10                  15

<210> SEQ ID NO 31
<211> LENGTH: 59
<212> TYPE: PRT
<213> ORGANISM: Bacillus subtilis
<300> PUBLICATION INFORMATION:
<301> AUTHORS: Schubert HL, Hill CP
<302> TITLE: Structure of ATP-bound human ATP:cobalamin
      adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (17)..(68)

<400> SEQUENCE: 31

Gly Arg Thr Asp Lys Asp Ser Leu Arg Val Glu Ser Tyr Gly Thr Ile
1               5                   10                  15

Asp Glu Leu Asn Ser Phe Ile Gly Leu Ala Leu Ala Glu Leu Ser Gly
            20                  25                  30

Gln Pro Gly Phe Glu Asp Leu Thr Ala Glu Leu Leu Thr Ile Gln His
        35                  40                  45

Glu Leu Phe Asp Cys Gly Gly Asp Leu Ala Ile
    50                  55

<210> SEQ ID NO 32
<211> LENGTH: 6
<212> TYPE: PRT
<213> ORGANISM: Bacillus subtilis

<400> SEQUENCE: 32

Val Thr Glu Arg Lys Asp
1               5

<210> SEQ ID NO 33
<211> LENGTH: 59
<212> TYPE: PRT
<213> ORGANISM: Bacillus subtilis
<220> FEATURE:
<221> NAME/KEY: misc_feature
<222> LOCATION: (58)..(58)
<223> OTHER INFORMATION: Xaa can be any naturally occurring amino acid
<300> PUBLICATION INFORMATION:
<301> AUTHORS: Schubert HL, Hill CP
<302> TITLE: Structure of ATP-bound human ATP:cobalamin
      adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (69)..(127)

<400> SEQUENCE: 33

Tyr Lys Leu Thr Arg Arg Ser Val Ser Phe Leu Glu Thr Arg Ile Asp
1               5                   10                  15

Ala Tyr Thr Glu Ala Glu Pro Glu Leu Lys Lys Phe Ile Leu Pro Gly
            20                  25                  30
```

```
Gly Ser Lys Cys Ala Ser Leu Leu His Ile Ala Arg Thr Ile Thr Arg
        35                  40                  45

Arg Ala Glu Arg Arg Val Val Ala Leu Xaa Lys
    50                  55

<210> SEQ ID NO 34
<211> LENGTH: 51
<212> TYPE: PRT
<213> ORGANISM: Bacillus subtilis
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (128)..(178)

<400> SEQUENCE: 34

Ser Glu Glu Ile His Glu Thr Val Leu Arg Tyr Leu Asn Arg Leu Ser
1               5                   10                  15

Asp Tyr Phe Phe Ala Gly Ala Arg Val Val Asn Ala Arg Ser Gly Ile
            20                  25                  30

Gly Asp Val Glu Tyr Glu Arg Ser Ala Ile Val Phe Arg Asp Asn Ser
        35                  40                  45

Ser Glu Ser
    50

<210> SEQ ID NO 35
<211> LENGTH: 16
<212> TYPE: PRT
<213> ORGANISM: Bacillus halodurans
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (1)..(16)

<400> SEQUENCE: 35

Arg Leu Tyr Thr Arg Thr Gly Asp Lys Gly Lys Thr Ser Val Ile Gly
1               5                   10                  15

<210> SEQ ID NO 36
<211> LENGTH: 58
<212> TYPE: PRT
<213> ORGANISM: Bacillus halodurans
<220> FEATURE:
<221> NAME/KEY: misc_feature
<222> LOCATION: (58)..(58)
<223> OTHER INFORMATION: Xaa can be any naturally occurring amino acid
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (17)..(74)
```

-continued

```
<400> SEQUENCE: 36

Gly Arg Leu Ala Lys Asp Asp Thr Arg Val Val Ala Tyr Gly Thr Thr
1               5                   10                  15

Asp Glu Leu Asn Ser Phe Val Gly Ser Ala Ile Thr Gln Leu Asp Glu
            20                  25                  30

Asn Thr Phe Ala Asp Ile Arg Gly Glu Leu Phe Lys Ile Gln His Glu
        35                  40                  45

Leu Phe Asp Cys Gly Gly Asp Leu Ala Xaa
        50                  55

<210> SEQ ID NO 37
<211> LENGTH: 25
<212> TYPE: PRT
<213> ORGANISM: Bacillus halodurans
<220> FEATURE:
<221> NAME/KEY: misc_feature
<222> LOCATION: (25)..(25)
<223> OTHER INFORMATION: Xaa can be any naturally occurring amino acid
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (75)..(99)

<400> SEQUENCE: 37

Thr Phe Ala Asp Ile Arg Gly Glu Leu Phe Lys Ile Gln His Glu Leu
1               5                   10                  15

Phe Asp Cys Gly Gly Asp Leu Ala Xaa
            20                  25

<210> SEQ ID NO 38
<211> LENGTH: 67
<212> TYPE: PRT
<213> ORGANISM: Bacillus halodurans
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188
<307> DATE: 2006-12-26
<313> RELEVANT RESIDUES IN SEQ ID NO: (100)..(166)

<400> SEQUENCE: 38

Leu Lys Val Lys Glu Asp Arg Pro Tyr Lys Ala Lys Gln Glu Ile Val
1               5                   10                  15

Asp Phe Leu Glu Gln Arg Ile Asp Ala Tyr Ile Lys Glu Ala Pro Glu
            20                  25                  30

Leu Glu Arg Phe Ile Leu Pro Gly Gly Ser Glu Ala Ala Ala Ser Leu
        35                  40                  45

His Val Cys Arg Thr Ile Ala Arg Arg Ala Glu Arg Tyr Val Val Arg
    50                  55                  60

Leu Gln Gln
65

<210> SEQ ID NO 39
<211> LENGTH: 54
<212> TYPE: PRT
<213> ORGANISM: Bacillus halodurans
```

```
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (167)..(220)

<400> SEQUENCE: 39

Glu Gly Glu Ile Asn Pro Ile Val Leu Lys Tyr Leu Asn Arg Leu Ser
1               5                   10                  15

Asp Tyr Phe Phe Ala Val Ala Arg Val Val Asn Ser Arg Leu Gln Val
            20                  25                  30

Pro Asp Val Glu Tyr Glu Arg Ser Ala Ile Val Phe Arg Glu Gly Lys
        35                  40                  45

Arg Lys Glu Asp Lys Lys
    50

<210> SEQ ID NO 40
<211> LENGTH: 149
<212> TYPE: PRT
<213> ORGANISM: Caenorhabditis elegans
<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (1)..(149)

<400> SEQUENCE: 40

Gly Phe Lys Gln Gly Arg Gly Thr Gly Asp Ser Gly Gln Ser Ser Leu
1               5                   10                  15

Tyr Asn Asn Glu Arg Arg Trp Lys Asp Asp Thr Phe Asn Ala Leu
            20                  25                  30

Gly Ala Thr Asp Glu Leu Ser Ser Phe Leu Gly Val Cys Gly Ala Ser
        35                  40                  45

Ala Gln Asn Asp Gly Ser Met Ser Asp Val Val Glu Thr Leu Thr Arg
    50                  55                  60

Leu Gln Cys Cys Leu Gln Asp Val Gly Ala His Leu Ala Thr Pro Pro
65                  70                  75                  80

Lys Asn Ser Ser Glu Arg Lys Gln Lys Lys Thr Ala Phe Asp Ile Ala
                85                  90                  95

Met Val Glu Trp Ile Asn Ala Glu Ile Asp Arg Tyr Gly Asp Ala Leu
            100                 105                 110

Pro Ala Ile Arg Gln Phe Ile Leu Ser Gly Gly Gly Met Thr Ser Ala
        115                 120                 125

Gln Leu Gln Tyr Ser Arg Ala Ile Cys Arg Arg Ala Glu Arg Ser Ile
    130                 135                 140

Val Pro Leu Met Arg
145

<210> SEQ ID NO 41
<211> LENGTH: 55
<212> TYPE: PRT
<213> ORGANISM: Caenorhabditis elegans
```

```
-continued

<300> PUBLICATION INFORMATION:
<301> AUTHORS: Schubert HL, Hill CP
<302> TITLE: Structure of ATP-bound human ATP:cobalamin
       adenosyltransferase.
<303> JOURNAL: Biochemistry
<304> VOLUME: 45
<305> ISSUE: 51
<306> PAGES: 15188-96
<307> DATE: 2006-12-26
<313> RELEVANT RESIDUES IN SEQ ID NO: (150)..(204)

<400> SEQUENCE: 41

Asp Glu Asp Val Asp Pro Met Ala Leu Lys Phe Leu Asn Arg Met Ser
1               5                   10                  15

Asp Leu Leu Phe Val Leu Gly Arg Thr Ala Cys Met Arg Asn Lys Asn
            20                  25                  30

Glu Glu Leu Thr Tyr Leu Arg Pro Asp Ser Phe Thr Asn Leu Lys Trp
        35                  40                  45

Asp Arg Lys Ser Leu His Glu
    50                  55
```

THERAPY OF NEUROLOGICAL INFLAMMATORY DISEASES WITH (5'-DEOXY-5'-ADENOSYL) COBAMAMIDE, RECOMBINANT HUMAN GROWTH HORMONE, INTERLEUKINS IL-1, IL-6, IL-11, EPIDERMAL GROWTH FACTOR, AND PHYSIOTHERAPY

CROSS-REFERENCE TO RELATED APPLICATIONS

There are no related applications.

FEDERALLY SPONSORED RESEARCH

Not Applicable

SEQUENCE LISTING OR PROGRAM

Herein, see pages 28-30

BACKGROUND OF THE INVENTION

1. Field of Invention

The present invention provides pharmaceutical compositions and methods of use for therapy of neurological inflammatory diseases with (5'-deoxy-5'-adenosyl)cobamamide, by itself or in combination with recombinant human growth hormone, Interleukins IL-1, IL-6, I'L-11, Epidermal Growth Factor, and physiotherapy.

2. Prior Art

The current generation of therapeutic agents and treatments for multiple sclerosis (MS) and other related neurological diseases seeks to reduce incidence and severity of lesions and to minimize clinical relapses. The current therapeutic methods have little effect on regeneration and remyelination. The etiology of demyelinating diseases is not well understood. Virtually all therapeutic agents were initially developed utilizing the Experimental Allergic Encephalomyelitis (EAE) animal model. The EAE animal model is an extreme example of central nervous system inflammation. When an etiological hypothesis is proposed, a therapy can be designed and implemented to address that proposed etiology. If the etiological hypothesis is essentially correct, then the implemented therapy will be effective. Without being restricted to any specific etiology, an original etiological hypothesis for MS is proposed and this provides a basis for therapeutic design. Specific therapeutic methods are described to address this etiological hypothesis. A scoping experiment in therapy, addressing a central feature of this hypothetical etiology, has been accomplished with a clinically definite MS patient who is in the Secondary Progressive stage of MS (SPMS). The dramatic improvement in the patient's condition strongly supports the etiological hypothesis. The recovery of physical abilities lost years before may indicate that remyelination occurred. It is doubtful that the EAE animal model could well demonstrate the effectiveness of this therapy.

The Etiology of Multiple Sclerosis

Multiple sclerosis is an inflammatory demyelinating disease of the central nervous system (CNS). There is general agreement that MS is an autoimmune disease in which B cells, T cells, and macrophage immune system cells enter the CNS, after a breach of the blood brain barrier (BBB), and begin the inflammatory and demyelinating pathological process. There have been thousands of publications describing research on MS. However, none has convincingly identified the exogenous antigenic environmental factors that initiate the cascade of immune system events that ultimately becomes the MS disease state. Thus, the etiology of MS has remained unknown.

The accumulated research logically demands that there is a particular exogenous antigen, or a class of exogenous antigens, bearing responsibility for the fundamental and seminal CNS immune response that leads to the development of MS. This patent describes an etiological hypothesis, strongly supported by published research, which allows design of therapeutic methods for the control of and recovery from MS.

The hypothetical etiology of multiple sclerosis begins with an infection in the systemic circulatory system by microbes, wherein said microbes contain enzymes for the production of (5'-deoxy-5'-adenosyl) cobamide, which is referred to as 5'-deoxyadenosylcobalmin (AdoCbl). Some of the microbial enzymes that produce AdoCbl might be classified as adenosyltransferase enzymes. Said microbial enzymes are highly homologous to human ATP:Cob(I)alamin adenosyltransferase (referred to as adenosyltransferase or as ATR). Many bacteria produce and utilize AdoCbl, and therefore have numerous enzymes that bind AdoCbl, as does human ATR. When systemic B lymphocytes bind to a microbe, an Antigen Presenting Complex (APC) is formed after which a T-helper cell activates the B lymphocyte making it replication competent, and resulting in clonal expansion. Eventually, the microbe is destroyed, its cell wall and cytoplasmic membrane are ruptured and then enzymes from the interior of the microbe are released. The various enzymes are also bound by B lymphocytes thereby producing APCs, and ultimately resulting in clonal expansion of these B lymphocytes. An activated B lymphocyte produces immunoglobulins (Ig) commonly called antibodies. Placental mammals produce five different isotypes called IgA, IgD, IgE, IgG, and IgM. Antibodies to bacterial enzymes and/or viral antigens that are similar to human ATR are cross-reactive to human ATR. Thus, MS is an autoimmune disease, wherein the immune system attacks some part of the body, referred to as a self-antigen.

One fact demanding an exogenous antigen is the epidemiological hotspot in Olmstead County, Minnesota, with 177 cases of MS per 100,000 people, which is much higher than the expected 30 to 80 cases of MS per 100,000 people. Soybean production is the major agricultural business in Olmstead County. Soybeans are legumes. Legumes have root nodules with nitrogen fixing bacteria in a symbiotic relationship with the legume plant, especially bacteria in the genus *Rhizobium*. The Rhizobia bacteria produce and utilize AdoCbl. The bacterial enzymes are somewhat homologous to human ATR. Therefore, antibodies to the bacterial ATR-like enzymes will be cross-reactive to human ATR. A soil sample contains a large number of different bacteria. A person with a cut, which has been contaminated with soil, will thus have many B lymphocytes activated against the bacteria, and subsequent to the destruction of the bacteria, against the enzymes released from the interior of the bacteria.

There are many bacteria that have ATR-like enzymes and each enzyme might have antibodies produced to it, which are cross-reactive to human ATR. An example with IgG antibodies could be described as % homology to human ATR equals approximate % cross-reactive antibody to human ATR, where a fraction is used for each antibody's reactivity:

$$\frac{IgG\text{-}Bacillus\ subtilus}{IgG\text{-human }ATR}$$

In this example, *Bacillus subtilus* is 41% homologous to ATR and the fractional representation in decimal form would be 0.41. Actual cross-reactivity may not be 41% as it depends on the active regions, but this is for discussion. Suppose there are four (4) ATR-like enzyme infections for which the immune system is on surveillance, $IgG_1=0.41$, $IgG_2=0.32$, $IgG_3=0.37$ and $IgG_4=0.39$. Thus, the cross-reactivity to ATR would be $$IgG_{ATR}=\Sigma 0.41+0.32+0.37+0.39=1.49$$

Any one bacterial IgG might not strongly react to ATR; however, the collection of IgGs is highly reactive to ATR. This cumulative effect could be a factor in the difficulty finding an exogenous antigen responsible for the development of MS. The ATR-like enzymes are a class of bacterial enzymes; therefore, there is not a single specific microbe, common to all MS patients. One other point may have obscured identification of an anti-ATR immune response. In the body, as a whole, the ATR enzyme is located predominantly in the interior of mitochondria. Therefore, the inner and outer membranes of the mitochondrion protect the ATR enzyme from an immune attack. Genetic diseases that impair the function of methylmalonyl-CoA mutase, for which AdoCbl is coenzyme, produce methylmalonic aciduria (MMA). Impaired production of AdoCbl in MS does not cause MMA. There may have been some expectation that AdoCbl deficiency would cause MMA. However, in the CNS, the ATR enzyme in glial cells may not be as well protected from immune attack because of the plasma membrane being permeable or even the ATR enzyme being extracellular. There are a number of metabolic reactions known in bacteria with AdoCbl functioning as coenzyme. There might be similar reactions occurring in human glial cells, which have not yet been discovered and described, for example an amino transferase function. Autoimmune attack of ATR as the initial molecular lesion leading to the development of MS has never been proposed in the published literature. No scoping experiment or clinical trial of AdoCbl for therapy of MS patients has ever been reported in the published literature. The dramatic therapeutic effect of AdoCbl, when administered to a clinically definite MS patient, strongly indicates that there is much not understood regarding the activity of AdoCbl in the CNS.

Next, in the etiological sequence, an event occurs, which causes a breach of the BBB. Immune system cells from the systemic circulatory system infiltrate into the CSF. Some of the B lymphocytes, having immunologic memory, are on surveillance for ATR-like antigens. These are activated against self-antigens in the CSF. These immune system cells bind ATR enzyme in the CSF, undergo clonal expansion, release antibodies, and begin a cascade of events to attack ATR. The CSF becomes deficient in ATR and, subsequently, the CSF becomes deficient in AdoCbl. AdoCbl is necessary for the formation of normal healthy myelin.

The reaction of methylmalonyl-CoA mutase, which requires AdoCbl as a coenzyme is shown in Scheme 1.

Scheme 1. Reaction of methylmalonyl-CoA mutase with AdoCbl as coenzyme.

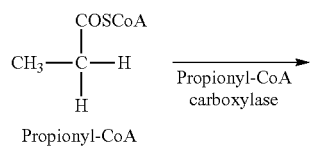

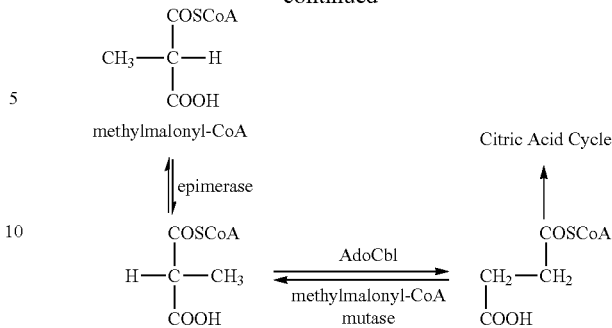

A lack of AdoCbl means that methylmalonyl-CoA and propionyl-CoA accumulate. Propionyl-CoA could then replace succinyl-CoA and act as a primer for fatty acid synthesis. This would result in the synthesis of odd carbon number fatty acids. These odd carbon number fatty acids could be inserted into myelin sheaths producing abnormal myelin, which is antigenic. Hydrolysis of methylmalonyl-CoA produces elevated levels of methylmalonic acid, which inhibits normal fatty acid synthesis. There are other major changes in the myelin of MS patients, such as hypomethylation and citrullination (deimination of arginine), which may result from a cascade of events subsequent to the reduction of the AdoCbl concentration. Another possibility is the failure of an amino transferase anabolic reaction, which gives the appearance that citrullination has occurred. The abnormal myelin is antigenic and is subject to attack by the immune system, but is never completely destroyed. The normal regulatory events do not occur that stimulate production of T suppressor cells. Poljakovic et al. (2006) reported that MS patients were 50% deficient in the concentration of growth hormone (GH) in the CSF. Zhang et al. (2006) reported that MS patients were deficient in the concentration of Interleukin-11. AdoCbl is a coenzyme for anabolic reactions in the CSF. It is probable that the reduced concentration of AdoCbl in the CSF is antagonistic to the normal synthesis of cytokines in the CSF, in a manner that is not fully understood. The strategy of therapy in this patent is to provide a normal or elevated concentration of AdoCbl and normal or elevated concentrations of growth hormone and other cytokines that are in reduced concentrations due to interference with their anabolic metabolism in the CSF. Cobalamin (Cbl) modulates synthesis of cytokines and growth factors. Cbl modulates in opposite ways the synthesis of the least Somme cytokines and growth factors. Therefore, these cytokines and growth factors can be defined as new cobalamin dependent CNS proteins, regardless of whether their synthesis increases or decreases in the presence of cobalamin.

Another AdoCbl reaction (called a MUT reaction) uses the adenosyl group from AdoCbl and methionine to produce S-adenosyl-methionine. The S-adenosyl-methionine is necessary for methylation of myelin sheath phospholipids. Failure of this reaction could result in the observed hypomethylation of myelin.

Failure of these reactions produces abnormal fatty acids, which can be incorporated into myelin. If the methylation of the myelin sheath phospholipids fails to occur, the resulting myelin will be fragile and antigenic. It is then subject to attack by the immune system causing demyelination. This may be referred to as conformational antigenicity.

There is a cascade of abnormal immune system events, stemming from the interaction of susceptibility genes, immune attack of ATR, deficiency of AdoCbl and some cytokines, an increase of necrosis factors, disturbance of anabolic metabolism thereby creating abnormal myelin, attack of abnormal myelin, etc. Ultimately, these events result in demyelination, oligodendrocyte death, axonal damage, and gliosis. The abnormal myelin likely has odd carbon number lipids, is hypomethylated, and has abnormal amination or deamination. Some B and T cells are activated against the abnormal myelin, because these immune cells, in the systemic blood system, may have been activated against similar viral or microbial antigens.

As the MS disease state progresses, an ascending peripheral neuropathy manifests with damage to axonal myelin and ultimately damage to denuded axons themselves. Loss of PNS myelin results in axonal death. In the CNS, the inflammation eventually becomes more diffuse and involves the whole brain with axonal injury and cortical demyelination.

Another fact demanding a logical explanation is the clinical similarity between subacute combined degeneration of the spinal cord and brain (SCD) and MS. SCD is a neurologic syndrome resulting from cobalamin (Vitamin $B_{12}$) deficiency. Clinically, it is difficult to differentiate SCD from MS. Scheme 2 shows the pathways leading to the $B_{12}$ coenzymes, AdoCbl and methylcobalamin (MeCbl).

Scheme 2. Production of Cobalamin Coenzymes.

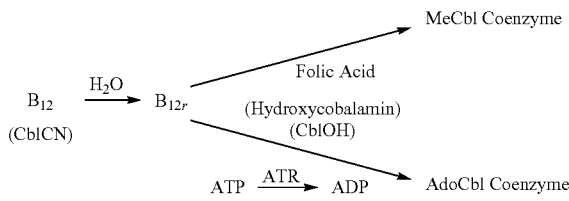

When the concentration of Vitamin $B_{12}$ is low, neither MeCbl nor AdoCbl are produced. The disease Pernicious Anemia results from failure to absorb Vitamin $B_{12}$ and is often accompanied by megaloblastic anemia and neurological lesions. SCD is caused by Vitamin $B_{12}$ deficiency and presents with neurological lesions and some anemia. SCD is treated by administration of Vitamin $B_{12}$ and this rectifies the anemia and neurological lesions. In therapy of SCD with Vitamin $B_{12}$ one clinical mistake is to also administer folic acid, which lessens anemia, but causes spinal cord lesions. The administration of folic acid decreases the AdoCbl concentration further by directing more Vitamin $B_{12}$ along the pathway to produce MeCbl and directing less Vitamin $B_{12}$ along the pathway to produce AdoCbl. This can be understood by consideration of Scheme 2. The fundamental and seminal CNS immune system event that leads to the development of MS is the autoimmune attack of ATR in the CSF. Consequently, Vitamin $B_{12}$ is not converted to AdoCbl, no matter what concentration of Vitamin $B_{12}$ is available.

Review of Neurological Inflammatory Diseases and Neurodegenerative Diseases

Neurological inflammatory diseases are widespread and include subacute combined degeneration of the spinal cord and brain (SCD) and multiple sclerosis (MS). SCD is a neurologic syndrome resulting from cobalamin (Vitamin $B_{12}$) deficiency. The SCD neurologic syndrome involves multiple nerve pathways, includes sclerotic lesions in CNS white matter, and widespread uneven degeneration of myelin in the spinal cord and eventually in the brain. The degeneration of myelin and formation of sclerotic lesions is an inflammatory process, typical of a response to an infection. The pathological changes of SCD result in numbness, paraparesis (loss of motor functions in the legs), tingling "pins and needles," clumsiness, unsteady gait, ataxia, and spasticity. Many of these neurologic abnormalities accompany pernicious anemia (PA), which results from extreme Vitamin $B_{12}$ deficiency. MS presents with symptoms such as motor weakness, paraparesis, visual impairment, ataxia, and bladder dysfunction. The variety of sensory effects often includes numbness and tingling sensations. Fatigue is common. The numerous symptoms result from the various locations of demyelination and inflammation in the brain. MS symptoms may be similar to or identical to the symptoms of other neurological inflammatory diseases, such as SCD. Magnetic Resonance Imaging (MRI) provides imaging of the sclerotic lesions distributed in the white matter and spinal cord. The MRI of a MS patient may look very much like the MRI of persons with other neurological inflammatory diseases. The cerebrospinal fluid (CSF) of a MS patient contains much immunoglobulin G (IgG), immunoglobulin M (IgM), and immunoglobulin A (IgA); these immunoglobulins indicate immune system involvement in the disease.

Neurodegenerative diseases actually include the neurological inflammatory diseases as well as disease states of the brain, spinal cord and peripheral nervous system. Examples would be the brain dysfunction and degeneration in Alzheimer Disease (AD) and Amyotrophic Lateral Sclerosis (ALS), which affects the peripheral nervous system. There are many other neurodegenerative disorders of the brain, spinal cord and peripheral nervous system. In general, the nervous system must have an adequate supply of Vitamin $B_{12}$ and more specifically its coenzymes MeCbl and AdoCbl. Several neurodegenerative disease states are known to result from deficiency in the concentration of Vitamin $B_{12}$ and its coenzymes, and such deficiency might be a factor in many other neurodegenerative diseases.

AdoCbl may be involved directly or indirectly in the synthesis of myelin components, other growth factors, cytokines and regulatory peptides in the CSF. Pezacka et al. (1992) cultured glial cells in cobalamin deficient medium for 6 weeks and then subcultured them with a cobalamin-rich medium; data was said to suggest that glial cells were exquisitely sensitive to short-term cobalamin deprivation after which the two major coenzymes were not produced. Poljakovic (2006) showed that the concentration of Growth Hormone in the CSF of MS patients was 50% lower than in control subjects.

U.S. Pat. No. 6,908,611, Cruz, et al. teaches the use of Vitamin $B_{12}$ compounds, including AdoCbl, in conjunction with "interferon compounds" to improve the effectiveness of the "interferon compounds" at a lower dose than normally administered. U.S. Pat. No. 6,908,611 does not teach that AdoCbl, by itself, provides effective therapy of MS and other neurological inflammatory diseases and neurodegenerative diseases, does not teach that AdoCbl facilitates remyelination, does not teach that AdoCbl stops secondary progression of disability in MS and allows extensive recovery from the symptoms of MS. U.S. Pat. No. 6,908,611 claims to demonstrate benefit in testing with the EAE animal model, but no human trials are provided, nor have human trials been reported in the literature.

U.S. Pat. No. 6,894,033, Cruz, et al. teaches the use of Vitamin $B_{12}$ compounds, including AdoCbl, in conjunction with anti-inflammatory, anti-viral and anti-proliferative compounds to improve the effectiveness of the therapeutic compounds at a lower dose than normally administered. U.S. Pat. No. 6,894,033, does not teach that AdoCbl, by itself, provides effective therapy of MS and other inflammatory diseases, does not teach that AdoCbl facilitates remyelination, does not teach that AdoCbl stops secondary progression of disability in MS and allows extensive recovery from the symptoms of MS. U.S. Pat. No. 6,894,033, claims to demonstrate benefit in testing with the EAE animal model, but no human trials are provided, nor have been reported in the literature.

U.S. Pat. No. 7,368,531, Rosen and Rubin, teaches the use of human secreted polypeptides in conjunction with "therapeutics" (pharmaceutical compositions) for diagnosing and for treatment of diseases. Rosen and Rubin do not specify nor list the sequence for ATP: Cob (I) alamin adenosyltransferase (AdoCbl). Rosen and Rubin do list methionine adenosyltransferase, S-adenosylmethionine, the Interleukins IL-1, IL-1alpha, IL-1beta, IL-6, and IL-11. These compounds are not used in conjunction with AdoCbl. Rosen and Rubin do not teach that AdoCbl administered in combination with the Interleukins IL-1, IL-1alpha, IL-1beta, IL-6, and IL-11 is an effective therapeutic method for MS.

AdoCbl promotes and maintains myelination. Interleukins IL-1, IL-1alpha, IL-1beta, IL-6, and IL-11 also promote and maintain myelination. A deficiency in AdoCbl has the potential to cause a reduction in the production of Interleukins IL-1, IL-1 alpha, IL-1beta, IL-6, and IL-11. Therefore, the combination of AdoCbl and Interleukins IL-1, IL-1alpha, IL-1beta, IL-6, and IL-11 can be expected to cause remyelination and/or maintain myelination.

U.S. Pat. Nos. 7,199,098, 6,939,539, 6,620,847, 6,342,476, 6,362,161, 6,054,430, 5,981,589, and 5,800,808 all by Konfino et al. teach the modification and use of Copolymer-1 (a synthetic polypeptide analog of myelin basic protein (MBP), which is a natural component of the myelin sheath). These are based on U.S. Pat. No. 3,849,550 by Teitelbaum, et al.

These patents claim to demonstrate benefit in testing with the EAE animal model, and human trials have been reported in the literature. Copolymer-1's use for therapy of MS has been approved by the Food and Drug Administration (FDA). These patents do not teach that AdoCbl facilitates remyelination, do not teach that AdoCbl stops secondary progression of disability in MS and that AdoCbl allows extensive recovery from the symptoms of MS. Human trials have been reported in the literature demonstrating that Copolymer-1 is effective in lowering the rate of relapse in Relapsing Remitting Multiple Sclerosis (RRMS), but shows no effective benefit for the Chronic Progressive forms of MS.

Copolymer-1 (glatiramer acetate) is the acetate salts of synthetic polypeptides from four amino acids: (Glu-Ala-Lys-Tyr)$_x$-CH$_3$COOH and is analogous to MBP. Schubert and Hill (2006) indicate that four residues appear to bind to AdoCbl in the ATR enzyme. Several of the point mutations causing Methyl Malonic Aciduria (MMA) are in the 186 to 194 residue region. The binding sites include Gly 97, Ser 174, Arg 186, Arg 190, Arg 191, Gln 193, and Gln 234. Two regions of interest in this current patent are highly conserved; first is a sequence of five amino acids (Sequence 4 in the Sequence Listing) in the 190 to 194 amino acids RRAER=Arg-Arg-Ala-Glu-Arg and the second region includes additional amino acids totaling nine amino acids (Sequence 3 in the Sequence Listing) in the 186 to 194 region RAVCRRAER=Arg-Ala-Val-Cys-Arg-Arg-Ala-Glu-Arg.

The concept for two claims is to use these amino acids or these sequences to form synthetic polypeptides like Copolymer-1, referred to as Copolymer-3-ATR (3 types of amino acids) and referred to as Copolymer-5-ATR (5 types of amino acids). These sequences form a cleft on human ATR that binds AdoCbl. The rationale is that this sequence is invariant between all microbial, mouse, and human PduO class ATRs. Therefore, an antibody to this sequence should be cross reactive to human ATR. The mechanism of action by Copolymer-1 has been opined as causing the formation of protective antibodies. Any of Sequences 1 through 6 in the Sequence Listing could be used. The effectiveness of Copolymer-1 was first demonstrated on the EAE animal model. EAE may not be a suitable animal model to demonstrate effectiveness of these epitopes. The totally gastectomized (TGX) rat is possibly a suitable animal model to demonstrate effectiveness of these epitopes, despite the lack of autoimmune attack of ATR. An animal model of MS could be created by inoculation of a rat, or other animal with microbial ATR-like enzymes (Sequences 7 through 14 in the Sequence Listing), followed by injecting its blood into its cranial CSF and thereby inducing autoimmune attack of ATR. This MS animal model would be suitable to evaluate Copolymer-3-ATR and Copolymer-5-ATR. This MS animal model would be suitable to evaluate the effectiveness of AdoCbl therapy.

The compound defined for one claim is Copolymer-3-ATR, which is the acetate salts of synthetic polypeptides from three amino acids: arginine, alanine, and y-benzyl glutamate in a molar ratio of approximately 3:1:1, respectively. The second compound defined for a claim is Copolymer-5-ATR, which is the acetate salts of synthetic polypeptides from five amino acids: arginine, alanine, valine, S-acetamidomethyl cysteine, and y-benzyl glutamate in a molar ratio of approximately 4:2:1:1:1, respectively. It is synthesized by chemically polymerizing the five amino acids forming products with average molecular weights of 23,000 daltons (U.S. Pat. No. 3,849,550). The designed structure for Copolymer-3-ATR is (Arg-Arg-Ala-Glu-Arg)$_x$-CH$_3$COOH and is analogous to ATR. Copolymer-3-ATR may be prepared by methods known in the art, for example, the process disclosed in U.S. Pat. No. 3,849,550, wherein the N-carboxyanhydrides of alanine, y-benzyl glutamate and E-N-continued trifluoro-acetylarginine are polymerized at ambient temperature in anhydrous dioxane with diethylamine as initiator. The deblocking of the y-carboxyl group of the glutamic acid is effected by hydrogen bromide in glacial acetic acid and is followed by the removal of the trifluoroacetyl groups from the arginine residues by 1M piperidine. For the purposes of this application, the terms "ambient temperature" and "room temperature" should be understood to mean a temperature ranging from about 20 to 26 degree C.

The designed structure for Copolymer-5-ATR is (Arg-Ala-Val-Cys-Arg-Arg-Ala-Glu-Arg)$_x$-CH$_3$COOH and is analogous to ATR. Copolymer-5-ATR may be prepared by methods known in the art, for example, the process disclosed in U.S. Pat. No. 3,849,550, wherein the N-carboxyanhydrides of alanine and valine, S-acetamidomethyl cysteine, y-benzyl glutamate and E-N-trifluoro-acetylarginine are polymerized at ambient temperature in anhydrous dioxane with diethylamine as initiator. The deblocking of the y-carboxyl group of the glutamic acid is effected by hydrogen bromide in glacial acetic acid and is followed by the removal of the trifluoroacetyl groups from the arginine residues by 1M piperidine. The deblocking of the S-acetamidomethyl group from cysteine is accomplished with iodine. For the purposes of this application, the terms "ambient temperature" and "room temperature" should be understood to mean a temperature ranging from about 20 to 26 degree C.

The invention will be exemplified but not necessarily limited by the following examples.

EXAMPLE 1

Chromatographic Method of Preparation of Low-toxicity Copolymer-3-ATR Two batches of copolymer-3-ATR were prepared according to the methods known in the art, for example, U.S. Pat. No. 3,849,550. One batch was then subjected to chromatographic separation, as described below. A column for gel filtration, FRACTOGEL TSK HW55 (600.times.26 mm) was prepared in a Superformance 26 Merck cartridge according to the manufacturer's instructions. The column was equilibrated with water and acetone solution was injected for total volume determination. The column was equilibrated with 0.2M ammonium acetate buffer pH 5.0. 30 ml copolymer-3-ATR samples (20 mg/ml, in 0.2M ammonium acetate pH 5.0) were loaded on the column and fractions were collected every 10 minutes. A fraction having an average molecular weight of 7-8 KDa was isolated between 120-130 minutes (Batch A).

EXAMPLE 2

Chromatographic Method of Preparation of Low-toxicity Copolymer-5-ATR Two batches of copolymer-3-ATR were prepared according to the methods known in the art, for example, U.S. Pat. No. 3,849,550. One batch was then subjected to chromatographic separation, as described below. A column for gel filtration, FRACTOGEL TSK HW55 (600.times.26 mm) was prepared in a Superformance 26 Merck cartridge according to the manufacturer's instructions. The column was equilibrated with water and acetone solution was injected for total volume determination. The column was equilibrated with 0.2M ammonium acetate buffer pH 5.0. 30 ml copolymer-5-ATR samples (20 mg/ml, in 0.2M ammonium acetate pH 5.0) were loaded on the column and fractions were collected every 10 minutes. A fraction having an average molecular weight of 7-8 KDa was isolated between 120-130 minutes (Batch A).

ATR activity has been confirmed and structure described for a number of bacteria; examples are Sequences 7 through 14 in the Sequence Listing, which are from:
*Thermoplasma acidiphilum* 32% homology to human ATR
*Bacillus subtilis* 41% homology to human ATR
*Sulfolobus tokodii*
*Sulfolobus tokodii* ST1454
*Bacillus holoduras*
*Mycobacterium tuberculosis*
*Pyrococcus horikoshi*

It is possible to accomplish lysis of bacteria and isolate ATR-like enzymes and to confirm their ATR activity. As previously discussed, here are many bacteria that have ATR-like enzymes and each enzyme might have antibodies produced to it, which are cross-reactive to human ATR. An array of purified bacterial ATR-like enzymes could be utilized for immunoprecipitation of sera from MS patients with different forms of MS. Potentially this would be a diagnostic and prognostic tool. This concept shall be a claim.

Purification of AdoCbl by different types of chromatography, gel filtration, electrophoresis, affinity chromatography or a tandem combination of such methods to produce United States Pharmaceutical (USP) grade AdoCbl, 99.9+% pure and suitable for use in treatment of patients is necessary. Tandem combination of separation methods with affinity chromatography is novel for purification of AdoCbl.

Houghten, in U.S. Pat. No. 4,631,211 describes sequential solid phase peptide synthesis in a foraminous bag wherein the solid phase particles are larger than the foraminae of the bag, referred to as the Tea-bag SPPS method; it is possible to synthesize large quantities of synthetic peptides by this method. Carbondell, in U.S. Pat. No. 5,045,190 describes chromatographic apparatus in which a functional group is a ligand for affinity chromatography. Berg, in U.S. Pat. No. 6,410,697 describes a process for purifying interferons with a combination of gel filtration and tandem affinity chromatography; the affinity chromatography methods described are both ligand affinity chromatography and antibody affinity chromatography. This patent has described synthesis of Copolymer-3-ATR and Copolymer-5-ATR based on the peptide sequence that binds AdoCbl in the cleft of the ATR enzyme. The concept herein presented is to produce either or both of these peptide sequences by the Tea-bag SPPS method, and with the peptide still attached to the solid support to place these peptides in a chromatography column. Said chromatography column is capped by a porous polypropylene frit in which the pores are smaller than the support particles to which the synthesized peptides are attached. This chromatography column has a high binding affinity for AdoCbl, which facilitates purification of AdoCbl to USP standards. This concept for preparation of AdoCbl in high purity (making USP standards) shall be a claim.

The current patent, by Boucher, teaches the effective use of AdoCbl, by itself, for therapy of MS and other neurological inflammatory diseases and neurodegenerative diseases. The effectiveness in therapy of a clinically definite MS patient has been demonstrated. The MS Patient presented with optic neuritis and was diagnosed with Relapsing Remitting Multiple Sclerosis (RRMS) some 15 years ago by MRI and lumbar puncture allowing demonstration of polyclonal banding in the CSF. Approximately 10 years ago the MS Patient was deemed to be in the Secondary Progressive Multiple Sclerosis (SPMS) stage due to the unremitting accumulation of disability. The MS Patient had loss of memory, cognitive impairment, loss of balance, fatigue, nocturia, not able to lift right foot from the floor, not able to raise right hand, not able to write with the right hand or to use a computer keyboard with the right hand, not able to grip with the right hand, not able to eat with a fork in the right hand, had poor heat tolerance, and was marginally ambulatory with a rollator. The MS patient was more affected on the right side than on the left, which prevented the use of a manual wheelchair. A scoping experiment in therapy with daily injections of 1000 mcg of AdoCbl was initiated. After three days the MS Patient was able to raise his right hand above his head, for the first time in years. After three days, the injection size was increased to 5000 mcg of AdoCbl daily. The MS Patient had been making daily injections of 20 mg Copaxone, but these were stopped for about two months when the scoping experiment with daily injections of AdoCbl was initiated. The MS Patient has recovered memory, cognition, normal balance, does not experience fatigue, no longer has nocturia, has recovered some ability with the right leg, is able to write with the right hand, use a computer keyboard with that right hand, and eat with a fork in the right hand. The MS patient is ambulatory and does not need a wheelchair. Use of the right leg is not fully restored; the current patent by Boucher also teaches the therapeutic use of Krox-20, Krox-24, NAB-1, NAB-2, and Oct-6 to promote myelination in the peripheral nervous system. The current patent, by Boucher, teaches that AdoCbl, by itself, provides effective therapy of MS and other inflammatory diseases, that AdoCbl facilitates remyelination, that AdoCbl stops secondary progression of disability in MS and allows extensive recovery from the symptoms of MS. The scoping experiment in therapy with AdoCbl was intended as a test of the etiological hypothesis that the enzyme ATP: Cob (I) alamin adenosyltransferase (ATR) in the CSF was a target of the immune system, which was a major factor in the development of MS. The results of the scoping experiment in therapy strongly support the proposed etiological hypothesis. There are missing details, potentially. Therefore, this patent is not to be restricted to addressing the proposed etiological hypothesis, as other etiological processes are possible.

Prior art in the patent literature and in the published medical literature for therapy of MS has no example of therapy that stops and reverses the progressive accumulation of disability. The current patent, by Boucher, teaches a method of therapy that stops the accumulation of disability and substantially reverses disability. The effectiveness of this therapy has been demonstrated on a human patient using 98% pure AdoCbl, for more than one year.

There are patents that teach the use of Vitamin $B_{12}$ compounds for treatment of diseases. However, to date, there is only one scoping experiment, with this patent, demonstrating the therapeutic effect of 5'-deoxyadednosylcobalamin by itself.

SUMMARY

A novel etiological hypothesis is proposed for multiple sclerosis and potentially other inflammatory and/or neurodegenerative diseases in this patent, which serves as the basis for rational design of therapeutic strategies. The proposed hypothesis is the autoimmune attack of ATP: Cob (I) alamin adenosyltransferase (ATR), which causes failure to convert Vitamin $B_{12}$ into (5'-deoxy-5'-adenosyl) cobamide, (referred to as Coenzyme $B_{12}$ or as AdoCbl), resulting in a deficiency of AdoCbl. Many bacteria produce and utilize AdoCbl and therefore have enzymes that are homologous to ATR; said enzymes are potentially exogenous antigens causing the autoimmune attack of ATR. The reduced concentration of AdoCbl causes production of defective antigenic myelin that replaces normal myelin during metabolic turnover, and causes reduced production of cytokines such as growth hormone (GH) and various Interleukins that require AdoCbl (Coenzyme $B_{12}$) for their production. The deficiency of AdoCbl causes reduced production of S-adenosyl methionine in the CSF and failure of normal methylation reactions.

The present invention describes pharmaceutical compositions that include AdoCbl, Interleukins, GH, Krox-20, Krox-24, NAB-1, NAB-2, Oct-6, and other compounds for the treatment of MS, and other inflammatory and/or neurodegenerative diseases. The rationale of this therapeutic design is provision of AdoCbl, because its concentration in the CSF is reduced by the autoimmune destruction of ATR and provision of various cytokines that have lowered concentrations, transcription factors such as Krox-20, Krox-24, NAB-1, NAB-2, Oct-6, which are important for myelination and remyelination.

The structure of ATR has been published including the enzyme's amino acid sequence. The active site has been defined including identification of which amino acids form the binding site for AdoCbl. The binding site for AdoCbl in ATR is homologous to sites that bind AdoCbl in bacterial enzymes. The present invention describes the use of the amino acid sequence in ATR that binds AdoCbl to form pharmaceutical compounds analogous to Copolymer 1 (Copaxone).

The present invention also describes the use of bacterial ATR-like enzymes for diagnostic tests by immunoprecipitation and other methods. An array of these tests has potential to diagnose types of MS and assist in making a prognosis.

A scoping experiment in therapy by parenteral injection of at a dose of between 1 µg and 2.5 g daily AdoCbl into a human subject with clinically definite MS in the secondary progressive stage was conducted. The subject regained physical abilities lost years before, regained memory and cognitive abilities, and had complete recovery from many common symptoms of MS such as fatigue and poor balance. Continuation of AdoCbl injections was found necessary to prevent relapse to the common symptoms of MS. AdoCbl administration stopped and reversed chronic progression of MS.

CONCLUSION, RAMIFICATIONS, AND SCOPE OF INVENTION

Normally, a person ingests Vitamin $B_{12}$ after which it is converted into methylcobalamin via a pathway that involves folic acid (and other enzymes) or it is converted into adenosylcobalmin (AdoCbl) by the ATP dependent enzyme adenosyltransferase (ATR). However, persons who have antibodies to ATR (persons with Multiple Sclerosis, for example) do not have a viable metabolic pathway to produce AdoCbl. Therefore, their body does not produce normal amounts of AdoCbl. Because of the deficiency of AdoCbl, the anabolic metabolic pathways that produce various cytokines are not operating properly. Because of the deficiency of AdoCbl, defective myelin is produced and slowly replaces normal myelin during metabolic turnover. Consequently, there is a cascade of events that results in the destruction of myelin in an inflammatory immune response to ATR enzyme and to the defective myelin. This patent describes pharmaceutical compositions to replace AdoCbl, interleukins important for maintenance of myelin, repair of myelin, and myelination in general, bacterial ATR-like enzymes for use in diagnostics of autoimmune response to ATR, and the preparation and use of compounds based on the active site in ATR enzyme.

The embodiments introduce a new rationale for therapeutic design and therapeutic strategies for treating demyelinating diseases. These include inhibition of immune attack on ATR and the promotion of remyelination and repair of myelin. In that the embodiments directly address the fundamental etiology of demyelinating inflammatory and neurodegenerative diseases, the embodiments offer the potential for the conquest of multiple sclerosis and related inflammatory and/or neurodegenerative diseases. A scoping experiment in therapy of a patient with clinically definite multiple sclerosis in the secondary progressive stage with AdoCbl demonstrated the effectiveness in stopping and even reversing the progressive accumulation of neurological damage due to multiple sclerosis. No therapy has ever been reported in the medical literature that can stop and reverse such progressive neurological damage.

The scope of the invention should be determined by the appended claims and their legal equivalents. The invention has been presented in the form of its preferred embodiments which are not intended as a limitation. The proposed etiological hypothesis is not intended as a limitation or restriction of this patent.

DEFINITIONS

Prior to setting forth the invention, it may be helpful to an understanding thereof to first set forth definitions of certain terms that will be used hereinafter.

"Neurological inflammatory diseases" means a class of diverse diseases and disorders that are characterized by any one of the following: the triggering of an inflammatory response, an upregulation of any member of the inflammatory cascade or the downregulation of any member of the inflammatory cascade. Neurological inflammatory diseases include Multiple Sclerosis, Alzheimer's Disease, Parkinson's Disease, Amyotrophic Lateral Sclerosis, and Poliomyelitis.

The singular term "neurological inflammatory disease" includes any one or more diseases selected from the class of neurological inflammatory diseases, and includes any compound or complex disease state wherein a component of the disease state includes a disease selected from the class of neurological inflammatory diseases.

| List of Immunomodulators (FDA approved drugs for therapy of MS) | | | |
|---|---|---|---|
| # | Prescribed drug | | |
| 4 | AVONEX | 30 mcg 10.5 mL kit | |
| 4 | BETASERON | 0.3 mg syringe | |
| 1 | Copaxone | 20 mg package = 30 Inj | |
| 12 | REBIF | 0.5 syringe Inj | |
| 10 | NOVATRONE | 2 mg/milliliter Inj | (Mitoxantrone) |
| 15 | TYSABRI | 300 mg/15 mL injection | |

Sequence Listing: Number of Seq Id Nos: 14
6 Sequences from Human Atp: Cob (I) Alamin Adenosyltransferase, (AAH05054.1) 244 Amino Acids Total

```
Sequence 1 (1-107), LENGTH: 107 Amino Acids
IPKIYTKTGDKGFSSTFTGERRPKDDQVFEAVGTTDELSSAIGFALELVT

EKGHT

Sequence 2 (110-185), 76 Amino Acids
CTLQDVGSALATPCSSAREAHLKYTTFKAGPILELEQWIDKYTSQLPPLT

AFILPSGGKISSALHFC

Sequence 3 (186-194), 9 Amino Acids
RAVCRRAER

Sequence 4 (190-194), 5 Amino Acids
RRAER

Sequence 5 (195-201), 7 Amino Acids
RVVPLVQ

Sequence 6 (204-244), 40 Amino Acids
MGETDANVAKFLNRLSDYLFTLARYAAMKEGNQEKIYKKNDPSAESEGL 8 Sequences from 8 Microbes with ATR-like
enzymes
Sequence from Pyrococcus horikoshi
Sequence 7
-----MRITTKVGDKGSTRLFGGEEVWKDSPIIEANGTLDELTSFIGEAK

HYVVD-----EEMKGILEEIONDIYKIMGEIGS--KGKIEG------ISE

ERIKWLEGLISRY-EEMVNLKSFVLPGGTLESAKLDVCRTIZRRAERKVA

TELR--EFGIGKEALVYLNRLSDLLFLLARVIEIEKNKLKEVRS

1 Sequence from Mycobacterium tuberculosis
Sequence 8
MAVHLTRIYTRTDGGDTTGLSDMSRVAKTDARLVAYADODEANAAIGAAL

ALGHPD---TQITDVLRQIQNDLFDAGADLSTPI--VENPKHPPLRIAQS

YIDRLEGWCDAYNAGLPALKSFVLPGGSPLSALLHVARTVVRRAERSAWA

AVDAHPEGVSVLPAKYLNRLSDLLFILSRVANPDGDVLWRPGGDRTAS--

----------

Sequence from Thermoplasma acidphilum
Sequence 9
-------MFTRRGDQGETDLANRARVGKDSPVVEVQGTIDELNSFIGYAL

VLSR----WDDIRNDLFRIQNDLFVLGEDVST----GGKGRT----VTRE

MIDYLEARVKEMKAEIGKIELFVVPGGSVESASLHMARAVSRRLERRIVA

ASK--LTEINKNVLIYANRLSSILFMHALISNKRLNIPEKIWWSIHRVS-

----------

Sequence from Sulfolobus tokodaii (St1454)
Sequence 10
---------FTKSGDDGNTNVIN-KRVGKDSPLNFLGDLDELNSFIGFAI

SKIP------WEDXKKDLERVQVELFEIGEDLST----QSKKK----IDE

KYVKWLEERTVEYRKESGPVKLFVIPGGSEEASVLHVTRSVARRVERNAV

KYTKE-LPEINRXIIVYLNRLSSLLFAXALVANKRRNVSEKIYDIGKFW-

----------

Sequence from Sulfolobus tokodaii (St2180)
Sequence 11
--------WYTGTGDKGKTKVPSVGEVWKDSEIVKALGDLDELNSVLGVV

SSLYP------ELSEVIQKLQNDIFSISSEIAG------FDXN----FSD

EKVKGIEELITNYSKELEPLRNFVLPGGHIASSFLHLARAVCRRAERSVV

TLLK--ESKAKEVHAKYLNRSSLLFVLALVVNKRTNNPNVIWRGKD----

-------

Sequence from Bacillus subtilis (Yvqk)
Sequence 12
------KLYTKTGDKGQTGLVG--GRTDKDSLRVESYGTIDELNSFIGLA

LAELSGQPGFEDLTAELLTIQHELFDCGGDLAI----VTERKD--YKLTR

RSVSFLETRIDAYTEAEPELKKFILPGGSKCASLLHIARTITRRAERRVV

ALXK--SEEIHETVLRYLNRLSDYFFAGARVVNARSGIGDVEYERSAIVF

RDNSSES---

Sequence from Bacillus halodurans (10174212)
Sequence 13
------RLYTRTGDKGKTSVIG-GRLAKDDTRVVAYGTTDELNSFVGSAI

TQLDEN-TFADIRGELFKIQHELFDCGGDLAX----LKVKEDRPYKAKQE

IVDFLEQRIDAYIKEAPELERFILPGGSEAAASLHVCRTIARRAERYVVR

LQQ--EGEINPIVLKYLNRLSDYFFAVARVVNSRLQVPDVEYERSAIVFR

EGKRKEDKK-

Sequence from Caenorhabditis elegans (AAA21165.2)
Sequence 14
----GFKQGRGTGDSGQSSLYNNERRWKDDDTFNALGATDELSSFLGVCG

ASAQNDGSMSDVVETLTRLQCCLQDVGAHLATPPKNSSERKQKKTAFDIA

MVEWINAEIDRYGDALPAIRQFILSGGGMTSAQLQYSRAICRRAERSIVP

LMR--DEDVDPMALKFLNRMSDLLFVLGRTACMRNKNEELTYLRPDSFTN

LKWDRKSLHE
```

I claim:

1. A method of treating a patient having a neurological inflammatory disease, the neurological inflammatory disease is selected form the group consisting of Multiple Sclerosis, Alzheimer's Disease, Parkinson's Disease, Amyotrophic Lateral Sclerosis, and Poliomyelitis, the method comprising administering to the patient (5'-deoxy-5'-adenosyl)cobamide (AdoCbl), at a dose of between 1 μg and 2.5 g daily.

2. A method of treating a patient having a neurological inflammatory disease, the neurological inflammatory disease is selected form the group consisting of Multiple Sclerosis, Alzheimer's Disease, Parkinson's Disease, Amyotrophic Lateral Sclerosis, and Poliomyelitis, the method comprising the steps of administering to the patient, either together or separately: (a) (5'-deoxy-5'-adenosyl)cobamide (AdoCbl), at a dose of between 1 μg and 2.5 g daily, as set forth in claim 1; and (b) recombinant human growth hormone.

3. A method of treating a patient having a neurological inflammatory disease, the neurological inflammatory disease is selected form the group consisting of Multiple Sclerosis, Alzheimer's Disease, Parkinson's Disease, Amyotrophic Lateral Sclerosis, and Poliomyelitis, the method comprising the steps of administering to the patient, either together or separately: (a) (5'-deoxy-5'-adenosyl)cobamide (AdoCbl), at a dose of between 1 μg and 2.5 g daily, as set forth in claim 1; and (b) physiotherapy.

4. A method of treating a patient having a neurological inflammatory disease, the neurological inflammatory disease is selected form the group consisting of Multiple Sclerosis, Alzheimer's Disease, Parkinson's Disease, Amyotrophic Lateral Sclerosis, and Poliomyelitis, the method comprising the steps of administering to the patient, either together or separately: (a) (5'-deoxy-5'-adenosyl)cobamide (AdoCbl), at a dose of between 1 μg and 2.5 g daily, as set forth in claim 1; and (b) Interleukin-11 (IL-11).

5. A method of treating a patient having a neurological inflammatory disease, as set forth in claim 1, the method comprising administering to the patient (5'-deoxy-5'-adenosyl)cobamide (AdoCbl), at a dose of between 1 μg and 2.5 g daily, wherein the patient has multiple sclerosis, and the route of administration is parenteral injection.

6. A method of treating a patient having a neurological inflammatory disease, the neurological inflammatory disease is selected form the group consisting of Multiple Sclerosis, Alzheimer's Disease, Parkinson's Disease, Amyotrophic Lateral Sclerosis, and Poliomyelitis, the method comprising the steps of administering to the patient, either together or separately: (a) (5'-deoxy-5'-adenosyl)cobamide (AdoCbl) at a dose of between 1 μg and 2.5 g daily, as set forth in claim 1; and (b) Interleukin-1 (IL-1).

7. A method of treating a patient having a neurological inflammatory disease, the neurological inflammatory disease is selected form the group consisting of Multiple Sclerosis, Alzheimer's Disease, Parkinson's Disease, Amyotrophic Lateral Sclerosis, and Poliomyelitis, the method comprising the steps of administering to the patient, either together or separately: (a) (5'-deoxy-5'-adenosyl)cobamide (AdoCbl) at a dose of between 1 μg and 2.5 g daily, as set forth in claim 1; and (b) Interleukin-6 (IL-6).

8. A method of treating a patient having a neurological inflammatory disease, the neurological inflammatory disease is selected form the group consisting of Multiple Sclerosis, Alzheimer's Disease, Parkinson's Disease, Amyotrophic Lateral Sclerosis, and Poliomyelitis, the method comprising the steps of administering to the patient, either together or separately: (a) (5'-deoxy-5'-adenosyl)cobamide (AdoCbl) at a dose of between 1 μg and 2.5 g daily, as set forth in claim 1; and (b) Epidermal Growth factor (EGF).

9. A method of treating a patient having a neurological inflammatory disease, the neurological inflammatory disease is selected form the group consisting of Multiple Sclerosis, Alzheimer's Disease, Parkinson's Disease, Amyotrophic Lateral Sclerosis, and Poliomyelitis, the method comprising the steps of administering to the patient, either together or separately: (a) (5'-deoxy-5'-adenosyl)cobamide (AdoCbl) at a dose of between 1 μg and 2.5 g daily, as set forth in claim 1; (b) recombinant human growth hormone, and (c) physiotherapy.

* * * * *